United States Patent
Cheng et al.

(10) Patent No.: US 9,116,135 B2
(45) Date of Patent: Aug. 25, 2015

(54) METHOD FOR DETECTING A SURFACE PATTERN OF A SOLAR CELL

(75) Inventors: Wen-Wei Cheng, Tao-Yuan Hsien (TW); Ming-Kai Hsueh, Tao-Yuan Hsien (TW); Wen-Chi Lo, Tao-Yuan Hsien (TW)

(73) Assignee: Chroma Ate, Inc., Tao-Yuan Hsien (TW)

( * ) Notice: Subject to any disclaimer, the term of this patent is extended or adjusted under 35 U.S.C. 154(b) by 553 days.

(21) Appl. No.: 13/469,193

(22) Filed: May 11, 2012

(65) Prior Publication Data
US 2013/0223747 A1  Aug. 29, 2013

(30) Foreign Application Priority Data

Feb. 29, 2012 (TW) .............................. 101106504 A

(51) Int. Cl.
*G06K 9/48* (2006.01)
*G01N 21/956* (2006.01)
*G01N 21/95* (2006.01)
*G06T 7/00* (2006.01)
*H01L 27/146* (2006.01)

(52) U.S. Cl.
CPC .......... *G01N 21/956* (2013.01); *G01N 21/9501* (2013.01); *G06T 7/0004* (2013.01); *G06T 2207/30148* (2013.01); *H01L 27/14601* (2013.01); *H01L 27/14603* (2013.01)

(58) Field of Classification Search
CPC ................. G01N 21/88; G01N 21/956; G06T 2207/30148; H01L 27/14601; H01L 27/14603
See application file for complete search history.

(56) References Cited

U.S. PATENT DOCUMENTS

| | | | | |
|---|---|---|---|---|
| 6,330,354 | B1* | 12/2001 | Companion et al. | 382/150 |
| 2005/0244049 | A1* | 11/2005 | Onishi et al. | 382/141 |
| 2007/0140550 | A1* | 6/2007 | Li et al. | 382/159 |
| 2008/0101686 | A1* | 5/2008 | Sali et al. | 382/149 |
| 2008/0239319 | A1* | 10/2008 | Yamashita et al. | 356/394 |
| 2009/0177415 | A1* | 7/2009 | Hayashi et al. | 702/40 |
| 2010/0034455 | A1* | 2/2010 | Harada et al. | 382/141 |

OTHER PUBLICATIONS

Van Kampen "Stochastic Processes in Physics and Chemistry", p. 27 (7."Central Limit Theorem").*

* cited by examiner

*Primary Examiner* — Chan Park
*Assistant Examiner* — Elisa Rice
(74) *Attorney, Agent, or Firm* — Rosenberg, Klein & Lee

(57) ABSTRACT

A surface pattern detecting method includes: capturing a surface image of a sample element to be detected, wherein the surface image containing N grayscale pixels and wherein the N is a positive integer; selecting f×N pixels with small grayscale value based on a selection ratio f in order to define a pattern zone and further calculating a pattern mean of the pattern zone based on pixel amount and grayscale value of the pattern zone; selecting f×N pixels with big grayscale value in order to define a background zone and further calculating a background mean of the background zone based on pixel amount and grayscale value of the background zone; and determining whether the surface image has a defect based on the pattern means of the pattern zone and the background mean of the background zone.

7 Claims, 7 Drawing Sheets

METHOD FOR DETECTING A SURFACE PATTERN OF A SOLAR CELL

This application claims the benefits of the Taiwan Patent Application Serial NO. 101106504 filed on Feb. 29, 2012, the subject matter of which is incorporated herein by reference.

BACKGROUND OF THE INVENTION

1. Field of the Invention

The present invention relates to an optical detecting method, more particularly to a method for detecting a surface pattern of a sample element.

2. Description of the Prior Art

In mass production industry, the manufactures always take great note how to pursuit high product quality and how to maintain the improved uniformity of a product. Therefore, in addition to alter the production process, the products produced accordingly must undergo quality detection in order to meet and satisfy the requirement demands of the consumers. In order to ensure an external appearance of a product is perfect or the product has no flaw or defect, the product must undergo a detection method during the mass production.

In several production fields, the finished product may have some specific surface pattern owing to restriction of the materials from which the product is manufactured. Even though the surface pattern does not affect the function quality of the product, but the non-uniform or irregular surface pattern fails to comply with the aesthetic demand of the consumers buying the product. Hence, degrading the cost quality of the product and may ultimately cause the consumer to request for refund of an already purchased product. Thus, if the defect of the product is not found out before the product is put on shelf for sale; this may cause extra expense in the production cost.

For instance, in the present trend of silicon solar cell production, it is relatively difficult to control the surface pattern of a crystal lattice owning to the production characteristics of a silicon wafer from which the solar cell is fabricated, hence causing each solar cell to possess the surface pattern different from another solar cell. The non-uniform surface pattern does not affect the function quality of the solar cell (i.e., does not hinder the production of electricity), but the uniform surface pattern in the solar cell still plays an important role once the solar cell is employed in a building system. Under this condition, the manufacturers should during the mass production detect out the underside defect of the surface pattern in a solar cell.

However, in the current pattern detection method, even though there is no unified standard for defining the surface pattern of a solar cell to meet the required standard, visual detection is utilized by those skilled personnel with their consciousness and personal experience in the mass production line to determine whether each of the solar cells has the uniform surface pattern relative to one another. Since the visual detection concept by an individual subjectivity differs from each other, there occurs the problem of misjudging uniform surface pattern in the solar cells. Under this condition, if the defect of the solar cells is not detected noticeably, the consumer may request for refund after purchasing the flaw products (i.e., the solar cells). Thus, the manufacturers have to shoulder an additional expense.

SUMMARY OF THE INVENTION

As described above, in the prior art surface pattern detecting method, there often occur the problem of misjudging the defect of the surface pattern since the detection of a surface pattern of a sample element is conducted by visual detection of an individual consciousness and personal experience. Since the visual detection concept by an individual subjectivity differs from each other, no unified standard can be defined; hence misjudging the defect of the surface pattern is often resulted.

Therefore, the main object of the present invention is to provide a surface pattern detection method, which can automatically find out the defect of a surface pattern of a sample element undergoing the detection, thereby eliminating the problem of misjudging the non-uniform surface pattern of the sample element conducted by visual detection according to the prior art technique.

The method of the present invention for detecting a surface pattern, includes the steps of: capturing a surface image of a sample element to be detected, wherein the surface image containing N grayscale pixels and wherein the N is a positive integer; and selecting f×N pixels with small grayscale value based on a selection ratio f in order to define a pattern zone and further calculating a pattern mean of the pattern zone based on pixel amount and grayscale value of the pattern zone.

At the same time, select f×N pixels with big grayscale value in order to define a background zone and further calculate a background mean of the background zone based on pixel amount and grayscale value of the background zone. Finally, determine whether the surface image of the sample element has a defect based on the pattern mean of the pattern zone and the background mean of the background zone. Preferably, the selection ratio f ranges from 0 to 0.5 and if the grayscale value contains N pixels indicates a normal distribution.

The detecting method of the present invention further includes a step of compiling a statistics containing pixel amount of each grayscale value and if the pixel amount of a respective one of the grayscale values is smaller than a predetermined amount, discount the pixel amount of the respective one of the grayscale values.

In one embodiment, the detecting method of the present invention further includes a step of determining the surface image of the sample element has the defect when a difference between the pattern mean of the pattern zone and the background mean of the background zone is greater than a predetermined difference.

In another embodiment, the detecting method of the present invention further includes a step of determining the surface image of the sample element has the defect when the pattern mean of the pattern zone is greater than a predetermined pattern value and when the pixel amount of the pattern zone is greater than a regional amount constituting the pattern zone.

In another embodiment, the detecting method of the present invention further includes a step of calculating a density of the pattern zone based on pixel distribution of the pattern zone, and determining the surface image of the sample element to have the defect when the density is greater than a predetermined density.

It is noted that the detecting method of the present invention is used to detect the surface pattern of a solar cell.

As explained above, when the detecting method of the present invention is utilized, the detection to the surface pattern of a sample element can achieve more precision so as to define a pattern zone and a background zone from the surface image owing to analyzing the grayscale values and characteristics of the surface pattern, determining whether a difference between the pattern mean of the pattern zone and the background mean of the background zone is greater than a predetermined difference and determining whether the density the pixels in the patter zone is greater than a default density, thereby determining whether the surface pattern undergoing the detection method of the present invention has the defect or free of the defect. When compared to the prior art method, where individual visual detection is utilized based on personal experience and personnel consciousness and subjectivity.

Hence utilization of the detecting method of the present invention can reduce the risk of misjudging the surface pattern and simultaneously reduces the production for the manufacturers.

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE PREFERRED EMBODIMENTS

The detecting method of the present invention is used for detecting a surface pattern of a sample element in order to analyze the grayscale value and characteristics of the surface image so as to determine whether the surface pattern has a flaw or defect. In order to better understanding of the present invention, a few examples are given in the following paragraphs. However, the scope of the present invention should not be limited to those given in the examples only.

Figure 1A:
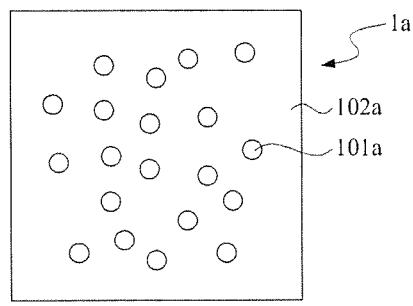
FIGS. 1A to 1E respectively show surface images with different grayscale values in accordance with the present invention.
Figure 1B:
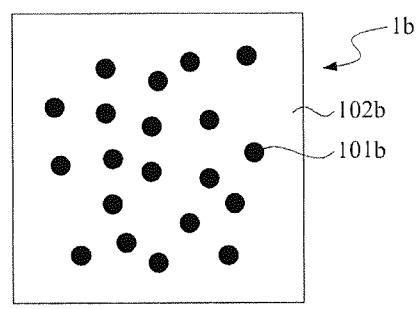
Figure 1C:
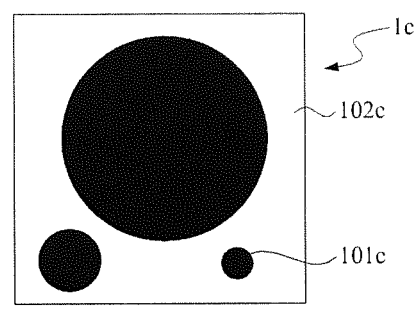
Figure 1D:
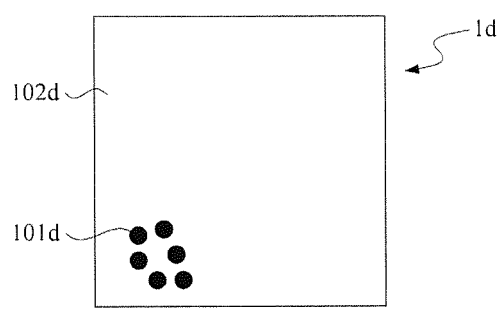
Figure 1E:
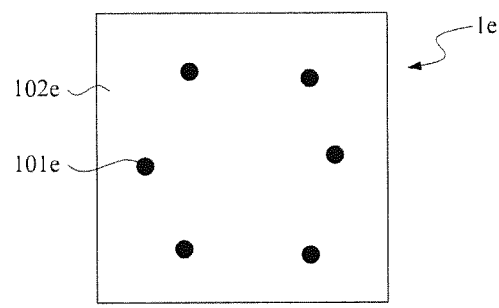
Figure 2:
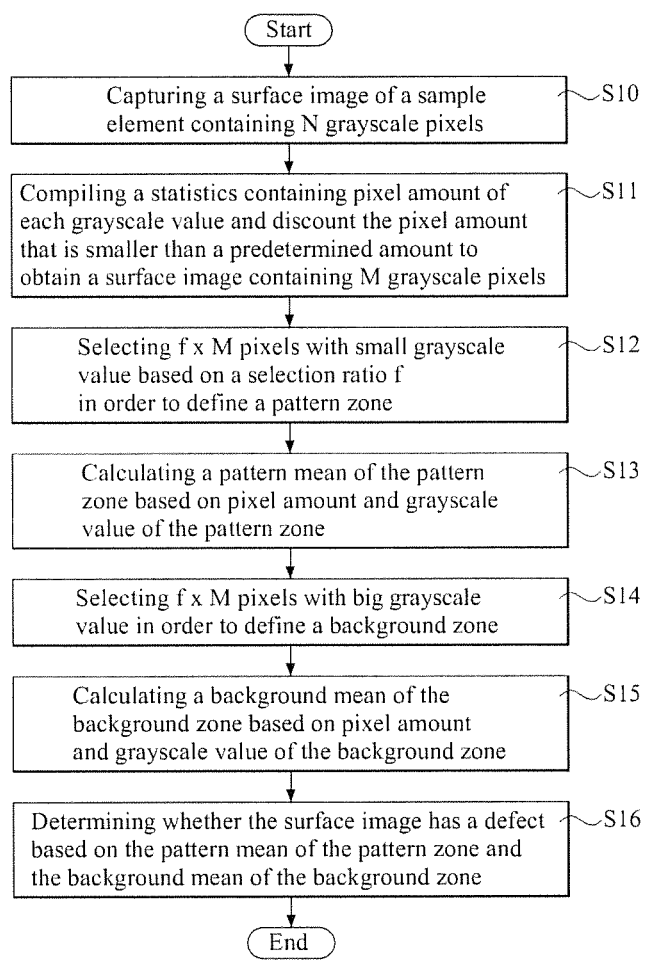
FIG. 2 is a block diagram illustrating the steps in the first method of the present invention for detecting the surface pattern of a sample element.
Figure 3:
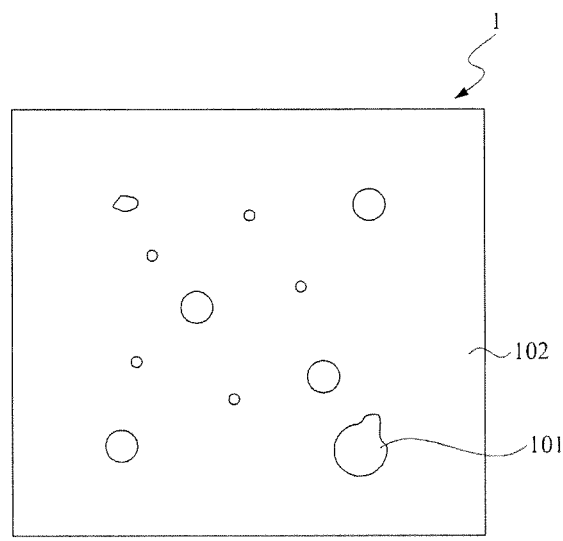
FIG. 3 shows a surface image of the sample element with grayscale values for undergoing the detecting method of the present invention.
Figure 4:
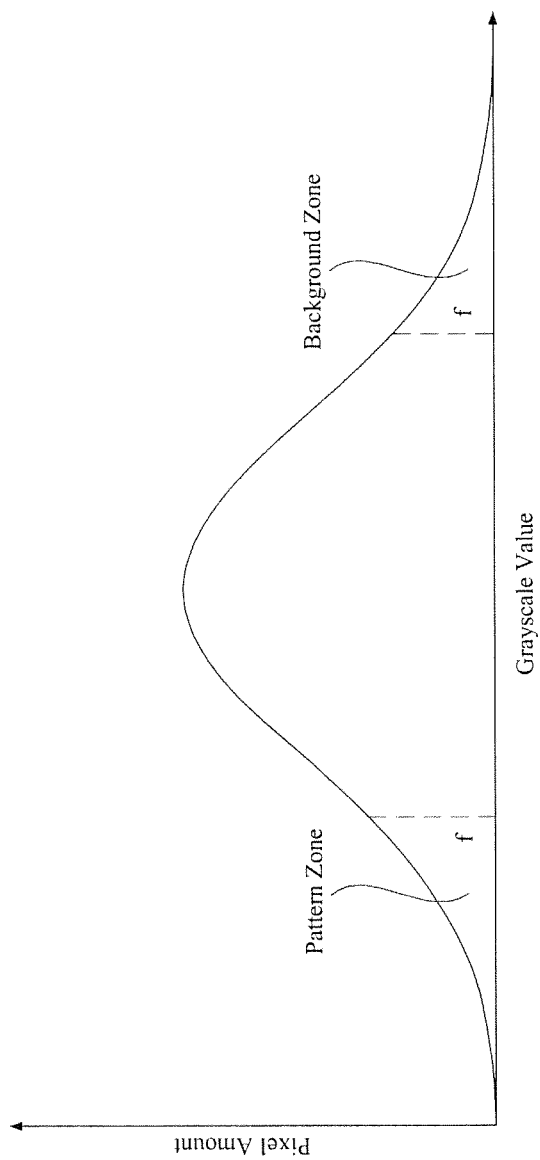
FIG. 4 shows a histogram illustrating the grayscale values relative to pixel amount of a surface image of the sample element in the detecting method of the present invention.

Referring to FIGS. 2 to 4, wherein FIG. 2 is a block diagram illustrating the steps in the first method of the present invention for detecting the surface pattern of a sample element; FIG. 3 shows a surface image of the sample element with grayscale values for undergoing the detecting operation according to the method of the present invention; while FIG. 4 shows a histogram illustrating the grayscale values relative to pixel amount of the surface image of the sample element in the detecting method of the present invention. Preferably, the sample element to be detected is a solar cell in the present invention. The detecting method of the present invention includes the following steps. In accordance with the step S10: a surface image of a sample element to be detected is captured and if the surface image containing N grayscale pixels and if the grayscale values of N pixels indicate that the grayscale value is a normal distribution. Preferably, N is a positive integer. In accordance with the step S11: compiling a statistics containing pixel amount of each grayscale value and if the pixel amount of a respective one of the grayscale values is smaller than a predetermined amount, discount the pixel amount of the respective one of the grayscale values, thereby obtaining a surface image 1 (1A, 1B, 1C and 1D in FIGS. 1A~1E respectively) containing M grayscale pixels, wherein M is smaller than N.

In accordance with the step S12: f×M pixels with small grayscale value is selected based on a selection ratio f in order to define a pattern zone 101. In this embodiment, the selection ratio f is 0.2. Then proceed to the step S13, where a pattern mean of the pattern zone 101 is calculated based on pixel amount and grayscale value of the pattern zone 101. In accordance with the step S14: f×M pixels with big grayscale value are selected based on the selection ratio f in order to define a background zone 102. As best shown in FIG. 4, based on the selection ratio f, a pattern zone 101 and the background zone 102 are defined from the surface image 1 containing M pixels.

In accordance with the step S15: a background mean of the background zone 102 is calculated based on pixel amount and grayscale value of the background zone 102. Finally the step S16 is conducted to determine whether the surface image 1 of the sample element has a defect based on the pattern mean of the pattern zone 101 and the background mean of the background zone 102. The determining principle depends on the difference between the pattern mean of the pattern zone 101 and the background mean of the background zone 102 in order to find out non-uniform surface pattern of the surface image 1 of the sample element.

FIGS. 1A to 1E respectively show surface images with different grayscale values in accordance with the present invention. As illustrated in FIGS. 1A and 1B, even though the pattern zone 101a in FIG. 1A has the same amount of regions (constituting a respective one of the pattern zone) as the pattern zone 101b in FIG. 1B, but the pattern zone 101b in FIG. 1B is more noticeable when compared to the background zone 102b in FIG. 1A. Therefore, by visual detection, the surface pattern or pattern zone shown in FIG. 1B is more noticeable.

In addition to the above-mentioned facts, the noticeable degree of the pattern zone can be determined by the amount of regions constituting a respective pattern zone. As illustrated in FIGS. 1B and 1C, the pattern zone 101b in FIG. 1B is constituted by more regional amount when compared to the pattern zone 101c with lesser regions. Under this condition, by visual detection, the surface pattern or pattern zone shown in FIG. 1B is more noticeable.

The scattering position of the pattern zone is another factor to determine the noticeable degree of the pattern zone. As illustrated in FIGS. 1D and 1E, the pattern zone 101d, 101e in FIGS. 1D and 1E, each is constituted by the same amount of regions, but the regional amount (number of regions) constituting the pattern zone 101d in FIG. 1D are located densely relative to one another when compared to the regions constituting the pattern zone 101e in FIG. 1E. Under this condition, by visual detection, the surface pattern or pattern zone shown in FIG. 1E is more noticeable.

Figure 5:
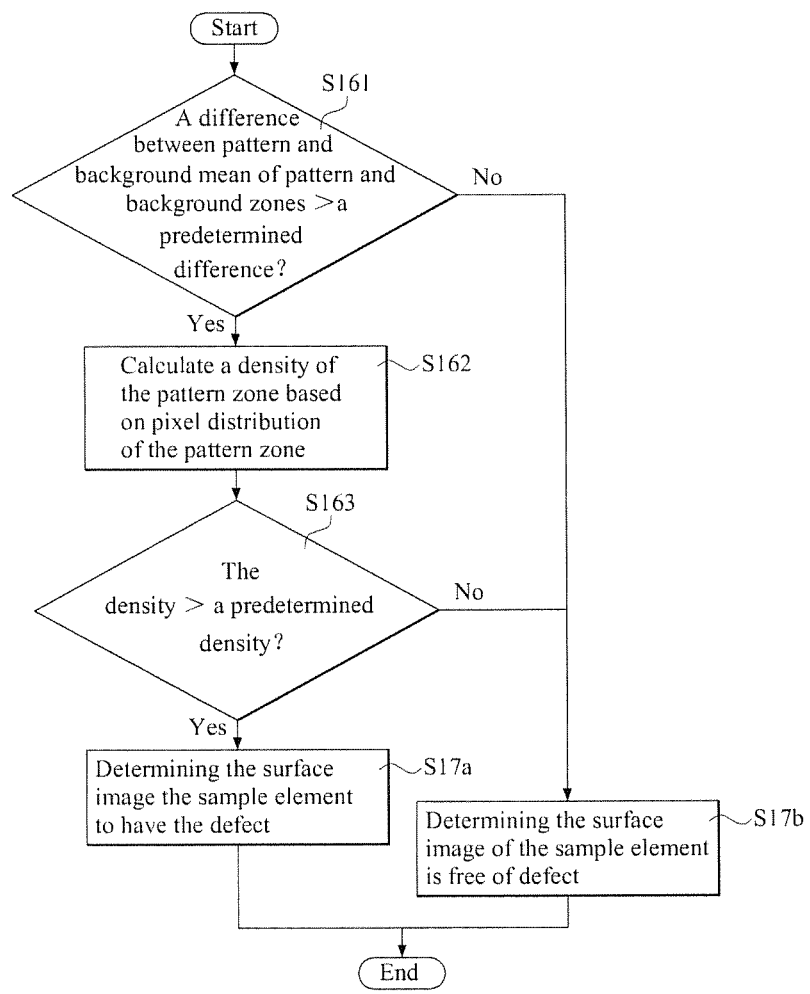
FIG. 5 is a block diagram illustrating the steps in the second method of the present invention for detecting the surface pattern of a sample element.

Referring to FIGS. 2 and 5, wherein FIG. 2 is a block diagram illustrating the steps in the first method of the present invention for detecting the surface pattern of a sample element while FIG. 5 is a block diagram illustrating the steps in the second method of the present invention for detecting the surface pattern of a sample element. As shown in FIG. 5, the step S16 further includes a substep S161: determine whether a difference between the pattern mean of the pattern zone and the background mean of the background zone is greater than a predetermined difference. If the difference between the pattern mean of the pattern zone and the background mean of the background zone is greater than the predetermined difference, proceed to the step S162, where the surface pattern (the pattern zone) of the sample element is determined to have the defect. If the difference between the pattern mean of the pattern zone and the background mean of the background zone is smaller than the predetermined difference, proceed to the step S17b, where the surface pattern (the pattern zone) of the sample element is determined to have no defect.

In the step S162, the density of the pixels in the pattern zone is calculated based on pixel distribution of the pattern zone. In the step S163, when the density is greater than a default density, then proceed to the step S17a, where the surface image (or surface pattern) of the sample element is determined to have the flaw or the defect. In accordance with the step S17b, when the density is smaller than the default density, the surface image (or surface pattern) of the sample element is determined to have no flaw or free of defect.

Figure 6:
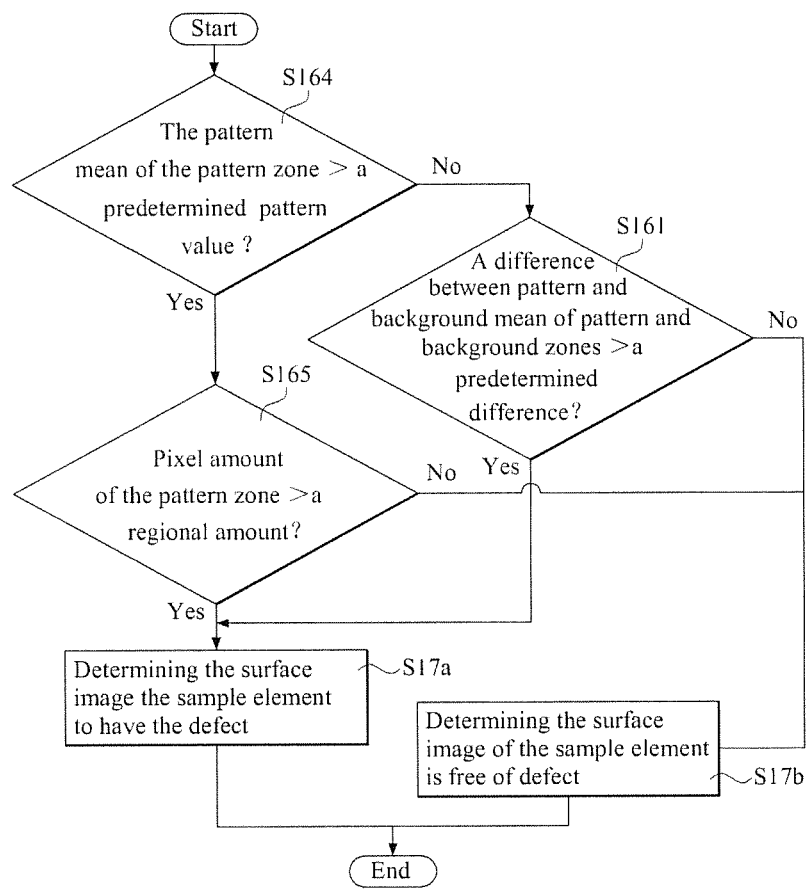
FIG. 6 is a block diagram illustrating the steps in the third method of the present invention for detecting the surface pattern of a sample element.

Referring to FIGS. 2 and 6, wherein FIG. 6 is a block diagram illustrating the steps in the third method of the present invention for detecting the surface pattern of a sample element. As illustrated in FIG. 6, the step S16 further includes a substep S164: determine whether the pattern mean of the pattern zone is greater than a predetermined pattern value. If the pattern mean of the pattern zone is greater than the predetermined pattern value, the detecting step enters into the step S165. If the pattern mean of the pattern zone is smaller than the predetermined pattern value, the detecting step goes back into the step S161.

In the step S165: determine whether the pixel amount of the pattern zone is greater than the number of the regions and if the pixel amount of the pattern zone is greater than the number of the regions, the detecting process enters into the step S17a, where the surface pattern of the sample element is determined to have the defect. If the pixel amount of the pattern zone is smaller than the number of the regions, the detecting process enters into the step S17b, where the surface image (surface pattern) of the sample element is determined to be free of defect.

In the step S161: determine whether a difference between the pattern mean of the pattern zone and the background mean of the background zone is greater than the predetermined difference and if the difference therebetween is greater than the predetermined difference, the detecting process enters into the step S17a, where the surface pattern of the sample element is determined to have the defect. If the difference between the pattern mean of the pattern zone and the background mean of the background zone is smaller than the predetermined difference, the detecting process enters into the step S17b, where the surface image (surface pattern) of the sample element is determined to be free of defect.

The above-mentioned step S16 may further include the substeps S161, S162, S163, S164 and S165, the combination and sequence of these substeps are illustrated for examples only so long as the detecting steps can achieve the intended motives so that a detailed description thereof is omitted herein for the sake of brevity.

It is obvious for those skilled person in the art when the detecting method of the present invention is utilized, the detection to the surface pattern of a sample element can achieve more precision so as to define the unified standard of the surface pattern owing to analyzing the grayscale values and characteristics of the surface pattern, thereby determining whether the surface pattern undergoing the detection method of the present invention has the defect or free of the defect. When compared to the prior art method, where individual visual detection is utilized based on personal experience and personnel consciousness and subjectivity, where undesired misjudging the defect of the surface pattern is often resulted.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for detecting visual uniformity of a surface having a pattern comprising:
    capturing a surface image of the surface to be detected, wherein said surface image contains N grayscale pixels and wherein said N is a positive integer;
    compiling a statistic containing pixel amount of each grayscale value and if said pixel amount of respective ones of the grayscale values is smaller than a predetermined amount, discounting said pixel amount of the respective ones of the grayscale values to leave in said surface image only M grayscale pixels after discounting, wherein said M is smaller than said N;
    selecting f×M first fraction of pixels having smallest grayscale value content, based on a selection ratio f, said first fraction of pixels defining a pattern zone, and calculating a mean of the grayscale values within said pattern zone;
    selecting f×M second fraction of pixels having biggest grayscale value content, said second fraction of pixels defining a background zone, further calculating a mean of the grayscale values within said background zone; and
    determining the visual uniformity of the surface based on respective mean grayscale values of said pattern zone and said background zone comparatively within said captured surface image.

2. The method according to claim 1, wherein determining whether said surface image of said sample element has said defect based on said pattern mean of said pattern zone and said background mean of said background zone comprises determining said surface image of said sample element has said defect when a difference between said pattern mean of said pattern zone and said background mean of said background zone is greater than a predetermined difference.

3. The method according to claim 1, wherein determining whether said surface image of said sample element has said defect based on said pattern mean of said pattern zone and said background mean of said background zone comprises determining said surface image of said sample element has said defect when said pattern mean of said pattern zone is greater than a predetermined pattern value and when said pixel amount of said pattern zone is greater than a regional amount.

4. The method according to claim 1, further comprising:
    calculating a density of said pattern zone based on pixel distribution of said pattern zone; and
    determining said surface image of said sample element to have said defect when said density is greater than a predetermined density.

5. The method according to claim 1, wherein said selection ratio f ranges from 0 to 0.5.

6. The method according to claim 1, wherein said sample element to be detected is a solar cell.

7. The method according to claim 1, wherein said grayscale values of N pixels indicate a normal distribution.

* * * * *